(12) United States Patent
Bauchet et al.

(10) Patent No.: US 12,361,731 B2
(45) Date of Patent: Jul. 15, 2025

(54) SYSTEMS AND METHODS FOR PREDICTING EXPRESSION LEVELS

(71) Applicant: Sanofi, Paris (FR)

(72) Inventors: Anne-Laure Bauchet, Paris (FR); Anthony Mei, Bridgewater, NJ (US); Qi Tang, Bridgewater, NJ (US)

(73) Assignee: Sanofi, Paris (FR)

( * ) Notice: Subject to any disclaimer, the term of this patent is extended or adjusted under 35 U.S.C. 154(b) by 346 days.

(21) Appl. No.: 17/911,841

(22) PCT Filed: Mar. 17, 2021

(86) PCT No.: PCT/US2021/022675
§ 371 (c)(1),
(2) Date: Sep. 15, 2022

(87) PCT Pub. No.: WO2021/188617
PCT Pub. Date: Sep. 23, 2021

(65) Prior Publication Data
US 2023/0143701 A1    May 11, 2023

Related U.S. Application Data

(60) Provisional application No. 62/991,412, filed on Mar. 18, 2020.

(30) Foreign Application Priority Data

Jun. 5, 2020 (EP) .................................... 20315297

(51) Int. Cl.
*G06V 20/69* (2022.01)
*G06T 7/00* (2017.01)
(Continued)

(52) U.S. Cl.
CPC .......... *G06V 20/695* (2022.01); *G06T 7/0012* (2013.01); *G06T 7/11* (2017.01);
(Continued)

(58) Field of Classification Search
CPC .... G06V 20/695; G06V 10/82; G06T 7/0012; G06T 7/11; G06T 2207/20021;
(Continued)

(56) References Cited

U.S. PATENT DOCUMENTS 11,783,604 B2 *  10/2023  Peng .................... G06V 20/69
                                                    382/133
2018/0330500 A1  11/2018  Sakurai et al.
(Continued)

FOREIGN PATENT DOCUMENTS

AU    2020421604 A1 *  8/2022  ......... G06K 9/00147
CN    111542830 A   *  8/2020  ............ G06N 20/00
(Continued)

OTHER PUBLICATIONS

Bychkov et al., "Deep learning based tissue analysis predicts outcome in colorectal cancer," Scientific Reports, Feb. 21, 2018, 8:3395, 11 pages.
(Continued)

*Primary Examiner* — Ted W Barnes
(74) *Attorney, Agent, or Firm* — Fish & Richardson P.C.

(57) ABSTRACT

One or more methods of predicting expression levels. At least one of the methods includes preprocessing image data representing at least one biological image of a patient to generate preprocessed image data representing at least one preprocessed biological image of the patient; and applying a trained machine learning model to the preprocessed image data to predict, based at least partially on the at least one preprocessed biological image, an expression level of a biological indicator.

20 Claims, 5 Drawing Sheets

(51) Int. Cl.
*G06T 7/11* (2017.01)
*G06V 10/25* (2022.01)
*G06V 10/75* (2022.01)
*G06V 10/82* (2022.01)
*G16H 50/20* (2018.01)

(52) U.S. Cl.
CPC .............. *G06V 10/25* (2022.01); *G06V 10/75* (2022.01); *G06V 10/82* (2022.01); *G06V 20/698* (2022.01); *G16H 50/20* (2018.01); *G06T 2207/20021* (2013.01); *G06T 2207/20081* (2013.01); *G06T 2207/20084* (2013.01); *G06T 2207/30096* (2013.01); *G06T 2207/30204* (2013.01)

(58) Field of Classification Search
CPC . G06T 2207/20081; G06T 2207/20084; G06T 2207/30096; G16H 50/20
See application file for complete search history.

(56) References Cited

U.S. PATENT DOCUMENTS

| | | | |
|---|---|---|---|
| 2019/0150857 A1 | 5/2019 | Nye et al. | |
| 2019/0206056 A1* | 7/2019 | Georgescu | G06T 7/0014 |
| 2019/0347557 A1* | 11/2019 | Khan | G06N 3/045 |
| 2019/0355113 A1* | 11/2019 | Wirch | G06T 7/32 |
| 2020/0321102 A1 | 10/2020 | Barnes et al. | |
| 2020/0394825 A1* | 12/2020 | Stumpe | G06F 18/214 |
| 2021/0073986 A1* | 3/2021 | Kapur | G06F 18/214 |
| 2021/0279875 A1* | 9/2021 | Saur | G06V 10/82 |
| 2021/0312620 A1* | 10/2021 | Zuo | G01N 1/30 |
| 2022/0130041 A1* | 4/2022 | Dogdas | G16H 10/40 |
| 2023/0419694 A1* | 12/2023 | Stumpe | G06T 11/001 |

FOREIGN PATENT DOCUMENTS

| | | | | |
|---|---|---|---|---|
| EP | 3729369 A2 * | 10/2020 | | G06T 7/0012 |
| EP | 3639191 B1 * | 9/2021 | | G01N 1/30 |
| JP | 2018-187384 A | 11/2018 | | |
| JP | 2019-093137 A | 6/2019 | | |
| WO | WO 2014/102130 | 7/2014 | | |
| WO | WO-2014102130 A1 * | 7/2014 | | G01N 33/57415 |
| WO | WO 2018/115055 | 6/2018 | | |
| WO | WO-2018115055 A1 * | 6/2018 | | G06K 9/0014 |
| WO | WO 2019/121564 | 6/2019 | | |
| WO | WO-2019121564 A2 * | 6/2019 | | G06T 7/0012 |
| WO | WO-2019172901 A1 * | 9/2019 | | G01N 1/30 |
| WO | WO-2019235828 A1 * | 12/2019 | | G06N 20/00 |
| WO | WO-2020014477 A1 * | 1/2020 | | |
| WO | WO-2021133847 A1 * | 7/2021 | | G06F 18/24137 |

OTHER PUBLICATIONS

DiMasi et al., "Innovation in the pharmaceutical industry: New estimates of R&D costs," Journal of Health Economics, May 2016, 47:20-33.
International Preliminary Report on Patentability in International Appln. No. PCT/US2021/022675, mailed Sep. 29, 2022, 11 page.
International Search Report and Written Opinion in International Appln. No. PCT/US2021/022675, mailed on Aug. 12, 2021, 16 pages.
Otsu, "A Threshold Selection Method from Gray-Level Histograms," IEEE Transactions on Systems, Man, and Cybernetics, Jan. 1979, SMC-9(1):62-66.
Sha et al., "Multi-Field-of-View Deep Learning Model Predicts Nonsmall Cell Lung Cancer Programmed Death-Ligand 1 Status from Whole-Slide Hematoxylin and Eosin Images," Journal of Pathology Informatics, Jul. 23, 2019, 1:24, 10 pages.
Shin et al., "Addressing the challenges of applying precision oncology," NPJ Precision Oncology, Sep. 4, 2017, 28:1-10.
Vamathevan et al., "Applications of machine learning in drug discovery and development," Nature Reviews Drug Discovery, Apr. 11, 2019, 18(6):463-477.
Xu et al., "GAN-based virtual re-staining: a promising solution for whole slide image analysis," CoRR, Submitted on Jan. 13, 2019, arXiv: 1901.04059v1, 16 pages.

* cited by examiner

SYSTEMS AND METHODS FOR PREDICTING EXPRESSION LEVELS

CROSS-REFERENCE TO RELATED APPLICATIONS

This application is the national stage entry of International Patent Application No. PCT/US2021/022675, filed on Mar. 17, 2021, which claims priority and benefit from U.S. Provisional Patent Application No. 62/991,412, filed Mar. 18, 2020 and European Patent Application No. 20315297.0, filed Jun. 5, 2020, the contents and disclosures of which are incorporated herein by reference in their entireties.

TECHNICAL FIELD

This disclosure generally relates to predicting expression levels of biological indicators, such as biomarkers.

BACKGROUND

A biological marker (or biomarker) is a measurable indicator of some biological state or condition. Biomarkers are often measured and evaluated to examine normal biological processes, pathogenic processes, or pharmacologic responses to a therapeutic intervention. Biomarkers can be used in many scientific fields. When a biomarker is qualified, analytically valid measurements of it can be relied upon to have a specific and interpretable meaning (for example, physiologic, toxicologic, pharmacologic, or clinical) in drug development and regulatory decision making.

Hematoxylin and eosin stain, or haematoxylin and eosin stain (H&E stain), can be one of the principal tissue stains used in histology. It can be used in medical diagnosis (for example, when a pathologist looks at a biopsy of a suspected cancer, the histological section is likely to be stained with H&E).

The cost of drug development has been rising since the 1990s and, on average, it cost approximately $2.6 billion in 2013 to bring a novel drug to market. In the era of precision medicine in oncology, for many clinical trials, patient's may only be enrolled if the immunohistochemistry (IHC) stained tumor biopsy samples are positive in terms of expression of a target biomarker according to a pre-specified threshold (for example, biomarker positive). The process of IHC screening a patient may take several days.

SUMMARY

In an aspect, a system is provided. The system includes a computer-readable memory comprising computer-executable instructions. The system includes at least one processor configured to execute the computer-executable instructions. When the at least one processor is executing the computer-executable instructions, the at least one processor is configured to carry one or more operations. The one or more operations include preprocessing image data representing at least one biological image of a patient to generate preprocessed image data representing at least one preprocessed biological image of the patient. The one or more operations include applying a trained machine learning model to the preprocessed image data to predict, based at least partially on the at least one preprocessed biological image, an expression level of a biological indicator.

The one or more operations can further include determining whether the predicted expression level of the biological indicator exceeds a threshold expression level. The one or more operations can further include determining, in response to determining that the predicted expression level exceeds the threshold expression level, to recommend performance of an immunohistochemistry (IHC) screening test for the patient. The one or more operations can further include determining, in response to determining that the predicted expression level does not exceed the threshold expression level, to not recommend performing the IHC screening test for the patient. The one or more operations can further include performing the IHC screening test for the patient to determine an IHC score. The one or more operations can further include determining, based at least partially on the determined IHC score, to enroll the patient in a clinical trial.

Preprocessing image data can include performing an automatic image thresholding process to segment one or more tissue regions of the biological image. Preprocessing image data can include applying a second trained machine learning model to the image data to virtually stain the at least one biological image, the second trained machine learning model trained to virtually stain the at least one biological image using an IHC image of the patient. Preprocessing the image data can include separating the at least one biological image into a plurality of image tiles. Preprocessing the image data can include separating each of the plurality of image tiles into a plurality of sub-tiles.

The at least one biological image can include at least one image of an hematoxylin and eosin (H&E) stain of the patient. The biological indicator can include a biomarker.

Implementations of the present disclosure can provide one or more of the following advantages. When compared with traditional techniques: the cost and time of clinical trial recruitment can be reduced; preprocessing of image data (for example, image tiling, image thresholding, virtual staining, and so on) can increase computational efficiency and accuracy of using machine learning models to make predictions; and prediction of continuous biomarker expression levels based on weakly labeled whole scans of H&E stained slides can be enabled.

These and other aspects, features, and implementations can be expressed as methods, apparatus, systems, components, program products, means or steps for performing a function, and in other ways.

These and other aspects, features, and implementations will become apparent from the following descriptions, including the claims.

DETAILED DESCRIPTION

Figure 1:
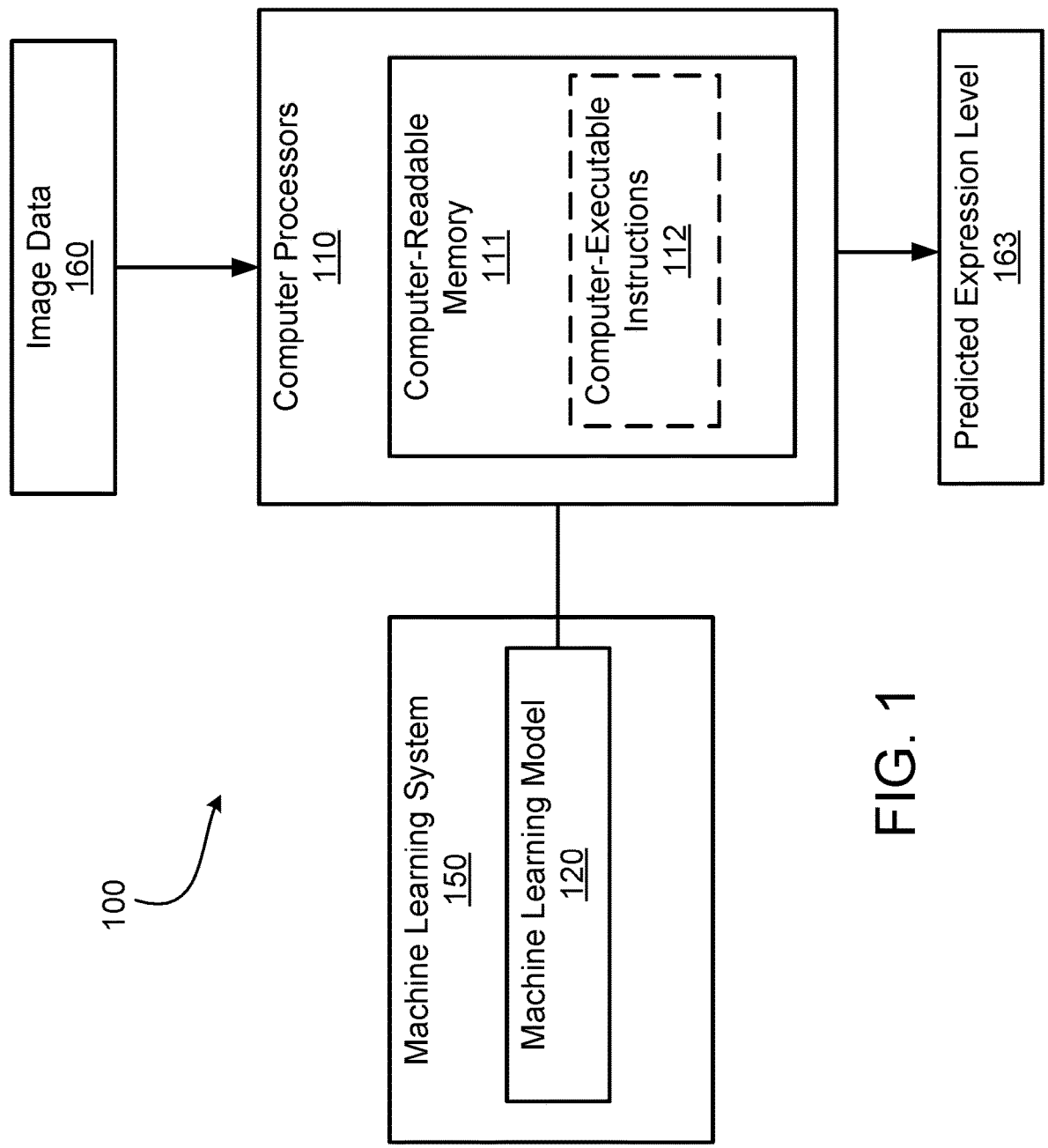
FIG. 1 is a block diagram illustrating an example system for predicting expression levels.

One bottleneck in drug development can be the identification of patients who are likely to meet the enrollment criteria for clinical trials, a process that may take months or years depending on the prevalence and size of the population of patients meeting the criteria. For instance, if the prevalence is only 50%, 100 patients may need to be screened on average to identify 50 patients meeting the criteria. Particularly, in the era of precision medicine in oncology, many clinical trials may require that patients only be enrolled if IHC stained tumor biopsy samples are positive in terms of expression of the target biomarker according to a pre-specified threshold (for example, biomarker positive). The process of IHC screening may take several days, which can slow down clinical trial recruitment, especially considering that a substantial percentage of the screened patients may not be biomarker positive.

Implementations of the systems and methods described in this specification can be used to alleviate one or more of the aforementioned disadvantages of traditional clinical recruitment techniques. In some implementations, the systems and methods described in this specification can use commonly available medical imaging data, such as H&E whole scan images of tumor samples from biopsy to predict patients' biomarker expression levels (for example, PD-L1 expression level for non-small cell lung cancer). In some implementations, unlike traditional machine learning approaches, which may use pixel-level (strongly) labeled images to predict biomarker expression status (classification), the systems and methods described in this specification can use machine learning techniques to enable the prediction of continuous biomarker expression levels (for example, through regression) based on weakly labeled whole images. In some implementations, the used images can be preprocessed to increase the accuracy and computational efficiency of the machine learning model in making predictions of biomarker expression levels.

In the drawings, specific arrangements or orderings of schematic elements, such as those representing devices, modules, instruction blocks and data elements, are shown for ease of description. However, it should be understood by those skilled in the art that the specific ordering or arrangement of the schematic elements in the drawings is not meant to imply that a particular order or sequence of processing, or separation of processes, is required. Further, the inclusion of a schematic element in a drawing is not meant to imply that such element is required in all implementations or that the features represented by such element may not be included in or combined with other elements in some implementations.

Further, in the drawings, where connecting elements, such as solid or dashed lines or arrows, are used to illustrate a connection, relationship, or association between or among two or more other schematic elements, the absence of any such connecting elements is not meant to imply that no connection, relationship, or association can exist. In other words, some connections, relationships, or associations between elements are not shown in the drawings so as not to obscure the disclosure. In addition, for ease of illustration, a single connecting element is used to represent multiple connections, relationships or associations between elements. For example, where a connecting element represents a communication of signals, data, or instructions, it should be understood by those skilled in the art that such element represents one or multiple signal paths (for example, a bus), as may be needed, to affect the communication.

Reference will now be made in detail to implementations, examples of which are illustrated in the accompanying drawings. In the following detailed description, numerous specific details are set forth in order to provide a thorough understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Several features are described hereafter that can each be used independently of one another or with any combination of other features. However, any individual feature may not address any of the problems discussed above or might only address one of the problems discussed above. Some of the problems discussed above might not be fully addressed by any of the features described herein. Although headings may be provided, data related to a particular heading, but not found in the section having that heading, may also be found elsewhere in this description.

FIG. 1 is a block diagram illustrating an example system 100 for predicting expression levels. The system 100 includes computer processors 110. The computer processors 110 include computer-readable memory 111 and computer readable instructions 112. The system 100 also includes a machine learning system 150. The machine learning system 150 includes a machine learning model 120. The machine learning system 150 may be separate from or integrated with the computer processors 110.

The computer-readable memory 111 (or computer-readable medium) can include any data storage technology type which is suitable to the local technical environment, including, but not limited to, semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In an implementation, the computer-readable memory 111 includes code-segment having executable instructions.

In some implementations, the computer processors 110 include a general purpose processor. In some implementations, the computer processors 110 include a central processing unit (CPU). In some implementations, the computer processors 110 include at least one application specific integrated circuit (ASIC). The computer processors 110 can also include general purpose programmable microprocessors, special-purpose programmable microprocessors, digital signal processors (DSPs), programmable logic arrays (PLAs), field programmable gate arrays (FPGA), special purpose electronic circuits, etc., or a combination thereof. The computer processors 110 are configured to execute program code means such as the computer-executable instructions 112. In some implementations, the computer processors 110 are configured to execute the machine learning model 120.

When executing the computer-executable instructions 112, the computer processors 110 are configured to receive image data 160 and generate, based on the image data 160, data representing a predicted expression level 163 of a target biological indicator (for example, a biomarker). The image data 160 can include data representing at least one biological image of a patient. In some implementations, the at least one biological image is an image of an H&E stained biological sample (for example, a tumor biopsy sample). H&E slide image files can include several resolutions of the H&E slide (for example, from 5 times of magnification to 20 times of magnification of cells). In some implementations, the image data 160 received by the computer processors 110 represents the images of cells having 20 times of magnification. Using higher resolution images can result in increased prediction accuracy of machine learning models (for example, the machine learning model 120). When executing the computer-executable instructions 112, the computer processors 110 are configured to preprocess the image data 160. In some implementations, preprocessing the image data 160 includes reducing the size of the image by segmenting certain tissues regions of the image from other portion of the image (for example, segmenting tumor tissue regions from other regions that include normal tissue and artifacts) using automatic image thresholding. In some implementations, Otsu's method is used to segment the tissue regions of the image, which can include applying an Otsu thresholding algorithm that returns a single intensity threshold that separates pixels into two classes, a foreground and a background. The algorithm can exhaustively search for the threshold that minimizes the intra-class variance, defined as a weighted sum of variances of the two classes according to the following formulation:

$$\sigma_\omega^2(t)=\omega_0(t)\sigma_0^2(t)+\omega_1(t)\sigma_1^2(t)$$

in which weights $\omega_0$ and $\omega_1$ are the probabilities of the two classes separated by a threshold t, and $\sigma0^2$ and $\sigma1^2$ are the variances of these two classes.

In some implementations, preprocessing the image data includes segmenting each tissue region into a plurality of tiles. Each of the tiles can correspond to a discrete portion of the original image. In some implementations, the original image includes a size of up to 40000×50000 pixels, which is segmented into tiles sizes of 1024×1024. In some implementations, the tiles may be further segmented into sub-tiles (patches) having sizes of, for example, 27×27. These sub-tiles can be centered around nuclei identified in the tiles using segmentation methods such as the Otsu thresholding algorithm discussed previously. In some implementations, preprocessing the image data includes receiving an IHC image of the patient, and applying a virtual staining machine learning model to virtually stain the H&E image using the IHC image, as discussed later with reference to FIG. 3. While both H&E stains and IHC stains refer to stains used in histopathology, IHC images can refer to images of "special" IHC stains that are more often used to identify expression of a specific protein, which can inform decisions of treating a patient (whereas H&E stains refer to stains that may be more often used for investigating underlying cellular and tissue structures). H&E stains may often be used as a tool for cancer diagnosis and can be available for many patients diagnosed with solid tumor, and the virtual staining machine learning model can be used to discover correlations between cell morphology exhibited in H&E stains with expression of a target protein in IHC stains. When executing the computer-executable instructions 112, and once the image data is preprocessed, the computer processors 110 are configured to apply the machine learning model 120 to the preprocessed image data.

The machine learning system 150 applies machine learning techniques to train the machine learning model 120 that, when applied to the input data, generates indications of whether the input data items have the associated property or properties, such as probabilities that the input data items have a particular Boolean property, an estimated value of a scalar property, or an estimated value of a vector (i.e., ordered combination of multiple scalars).

As part of the training of the machine learning model 120, the machine learning system 150 can form a training set of input data by identifying a positive training set of input data items that have been determined to have the property in question, and, in some implementations, forms a negative training set of input data items that lack the property in question.

The machine learning system 150 extracts feature values from the input data of the training set, the features being variables deemed potentially relevant to whether or not the input data items have the associated property or properties. An ordered list of the features for the input data is herein referred to as the feature vector for the input data. In some implementations, the machine learning system 150 applies dimensionality reduction (e.g., via linear discriminant analysis (LDA), principle component analysis (PCA), learned deep features from a neural network, or the like) to reduce the amount of data in the feature vectors for the input data to a smaller, more representative set of data.

In some implementations, the machine learning system 150 uses supervised machine learning to train the machine learning model 120 with the feature vectors of the positive training set and the negative training set serving as the inputs. Different machine learning techniques—such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps—are used in some implementations. The machine learning model 120, when applied to the feature vector extracted from the input data item, outputs an indication of whether the input data item has the property in question, such as a Boolean yes/no estimate, a scalar value representing a probability, a vector of scalar values representing multiple properties, or a nonparametric distribution of scalar values representing different ad no a priori fixed numbers of multiple properties, which may be represented either explicitly or implicitly in a Hilbert or similar infinite dimensional space.

In some implementations, a validation set is formed of additional input data, other than those in the training sets, which have already been determined to have or to lack the property in question. The machine learning system 150 applies the trained machine learning model 120 to the data of the validation set to quantify the accuracy of the machine learning model 120. Common metrics applied in accuracy measurement include: Precision=TP/(TP+FP) and Recall=TP/(TP+FN), where precision is how many the machine learning model 120 correctly predicted (TP or true positives) out of the total it predicted (TP+FP or false positives), and recall is how many the machine learning model 120 correctly predicted (TP) out of the total number of input data items that did have the property in question (TP+FN or false negatives). The F score (F score=2*PR/(P+R)) unifies precision and recall into a single measure. In some implementations, the machine learning system 150 iteratively re-trains the machine learning model 120 until the occurrence of a stopping condition, such as the accuracy measurement indication that the model 120 is sufficiently accurate, or a number of training rounds having taken place.

In some implementations, the machine learning model 120 includes a neural network. In some implementations, the neural network includes a convolutional neural network (CNN) architecture. A CNN generally describes a class of deep neural networks and can include a shared-weights architecture and translation invariance characteristics. In some implementations, the machine learning model includes a deep recurrent attention model (DRAM), which can refer to a neural network that includes a built-in degree of translation invariance, but the amount of computations performed can be controlled independently from the input image size. In some implementations, a DRAM includes a deep recurrent neural network trained with reinforcement learning to attend to the most relevant areas of large input patches (for example, the segmented tissue regions of the preprocessed image data discussed previously). In some implementations, the machine learning model 120 is developed using multiple-instances learning (MIL). MTh can refer to a type of supervised learning in which, instead of receiving a set of instances which are individually labeled, the machine learning model 120 receives a set of labeled "bags," each containing many instances. Each bag can either be labeled negative, indicating that all of the instances in it are negative, or positive, indicating that the bag includes at least one instance which is positive. From the collection of labeled bags, the machine learning model 120 can attempt to either induce a concept that will label individual instances correctly or learn how to label bags without inducing the concept.

The machine learning model 120 is configured to predict an expression level of a biological indicator (for example, a target biomarker) based on the biological image of the preprocessed image data 160 (that is, using the preprocessed image data). For example, if a clinical trial is directed to immunotherapy for non-small cell lung cancer, a target biomarker can include programmed death ligand 1 (PD-L1). Accordingly, in some implementations, the machine learning model 120 is configured to predict an expression level (for example, an expression score from 0 to 100) of PD-L1 exhibited by the patient based on the biological image.

To train the machine learning model 120 to predict expression levels of a biological indicator, the machine learning system 150 can apply the machine learning model 120 to a training set that includes biological images of a patient (for example, images of H&E stained slides) and known expression levels of the target biological indicator. The known expression levels of the target biological indicator can be manually produced by medical experts based on analyzing IHC stains. The machine learning model 120 can learn to associate certain features of the biological images with the known expression levels. Based on these associations, when the machine learning model 120 is applied to a new biological image, the machine learning model can predict an expression level of the target biological indicator using the learned associations. In some implementations, when training the machine learning model 120, the machine learning system 150 uses a directional loss function, which can optimize the model parameters to take advantage of continuous proportion scores while focusing on the target to be predicted. In some implementations, the direction loss function pushes the predicted values closed to the true values but also forces the prediction to yield the same biomarker status (that is, whether or not a target biomarker is present) as the true one. In some implementations, it achieves this goal by pushing an error more heavily if it yields a wrong biomarker status prediction. In some implementations, the loss function is defined as:

$$\Sigma_i(y_i-\hat{y}_i)^2((w_1-1)I(y_i>c)+1)((1-I(I(y_i>c)==I(\hat{y}_i>c)))(w_2-1)+1);$$

where $y_i$ and $\hat{y}_i$ refer to the observed and predicted target protein expression level in an IHC image for patient i, c refers to a threshold used in the clinical trial recruitment process where only patients with higher than the threshold expression level can be enrolled into the clinical trial, $w_1$ refers to the weight for the prediction loss of patients with true expression level greater than the threshold, and $w_2$ refers to the weight for the prediction loss of patients with predicted expression level on the opposite side of the threshold comparing to the true expression level. Setting $w_2$ to a value greater than one forces the model to learn features to yield predictions consistent with the true value in terms of classifying patients into high vs low expressions.

Figure 2:
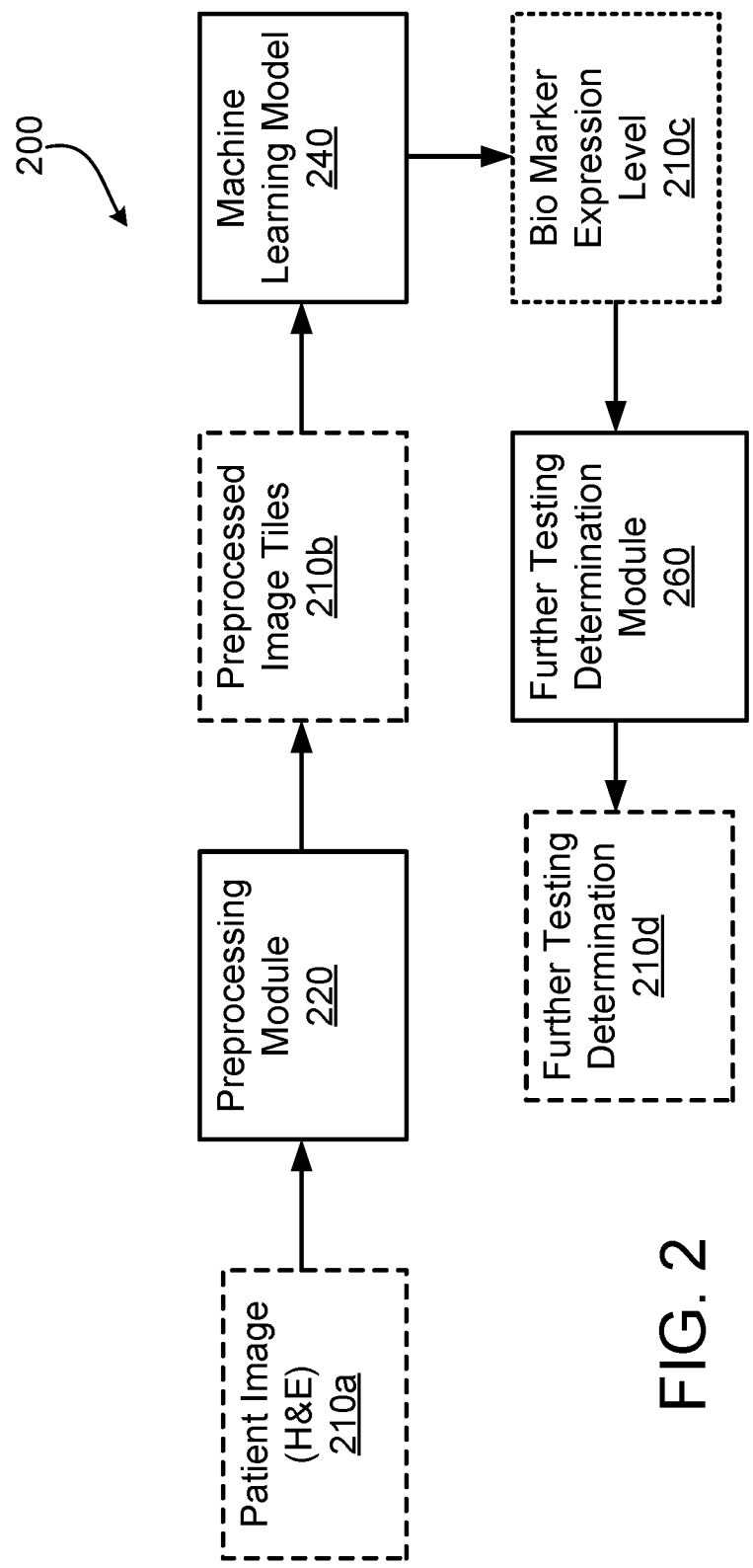
FIG. 2 is a flow diagram illustrating an example architecture for predicting expression levels.

FIG. 2 is a flow diagram illustrating an example architecture 200 for predicting expression levels. In some implementations, the computer processors 110 discussed previously with reference to FIG. 1 includes one or more components of the architecture 200. The architecture 200 includes a preprocessing module 220, a machine learning model 240, and a further testing determination module 260.

The preprocessing module 220 is configured to receive data representing one or more patient images 210a, and preprocess the image data to generate data representing preprocessed image tiles 210b. The one or more patient images 210a can include biological images, such as images of H&E stained slides of a patient undergoing screening for a clinical trial. Preprocessing includes splitting the image 210a into a plurality of image tiles 120b (and, as previously indicated, in some implementations, splitting the image tiles 120b into sub-tiles), in which each of the image tiles 210b (and/or sub-tiles) corresponds to a discrete portion of the image 210a. In some implementations, preprocessing includes applying an Otsu thresholding algorithm to the image data to segment certain tissue regions of the image 210a from other portions of the image 210a, as discussed previously with reference to FIG. 1.

The machine learning model 240 receives the preprocessed image tiles 210b (and/or sub-tiles in some implementations) and generates, based on the preprocessed image tiles 210b (and/or sub-tiles), data representing an expression level 210c (for example, on a scale of 0-100) of a target biomarker of the patient in accordance with one or more techniques described previously with reference to FIG. 1. The further testing determination module 260 receives the data representing the expression level 210c and generates data representing a further testing determination 210d. Generating data representing a further testing determination 210d includes comparing the biomarker expression level 210c with an expression level threshold (for example, 50). The expression level threshold can be based on one or more of: the precision of the machine learning model 240, the recall of the machine learning model 240, clinical trial design considerations, or regulatory standards, among others. If the biomarker expression level 210c exceeds the expression level threshold, the further testing determination 210d can indicate that the patient is recommended for further testing. If the biomarker expression level 210c does not exceed the expression level threshold, the further testing determination 210d can indicate that the patient is not recommended for further testing. Further testing can include performance of manual IHC screening by medical experts using IHC stains.

Figure 3:
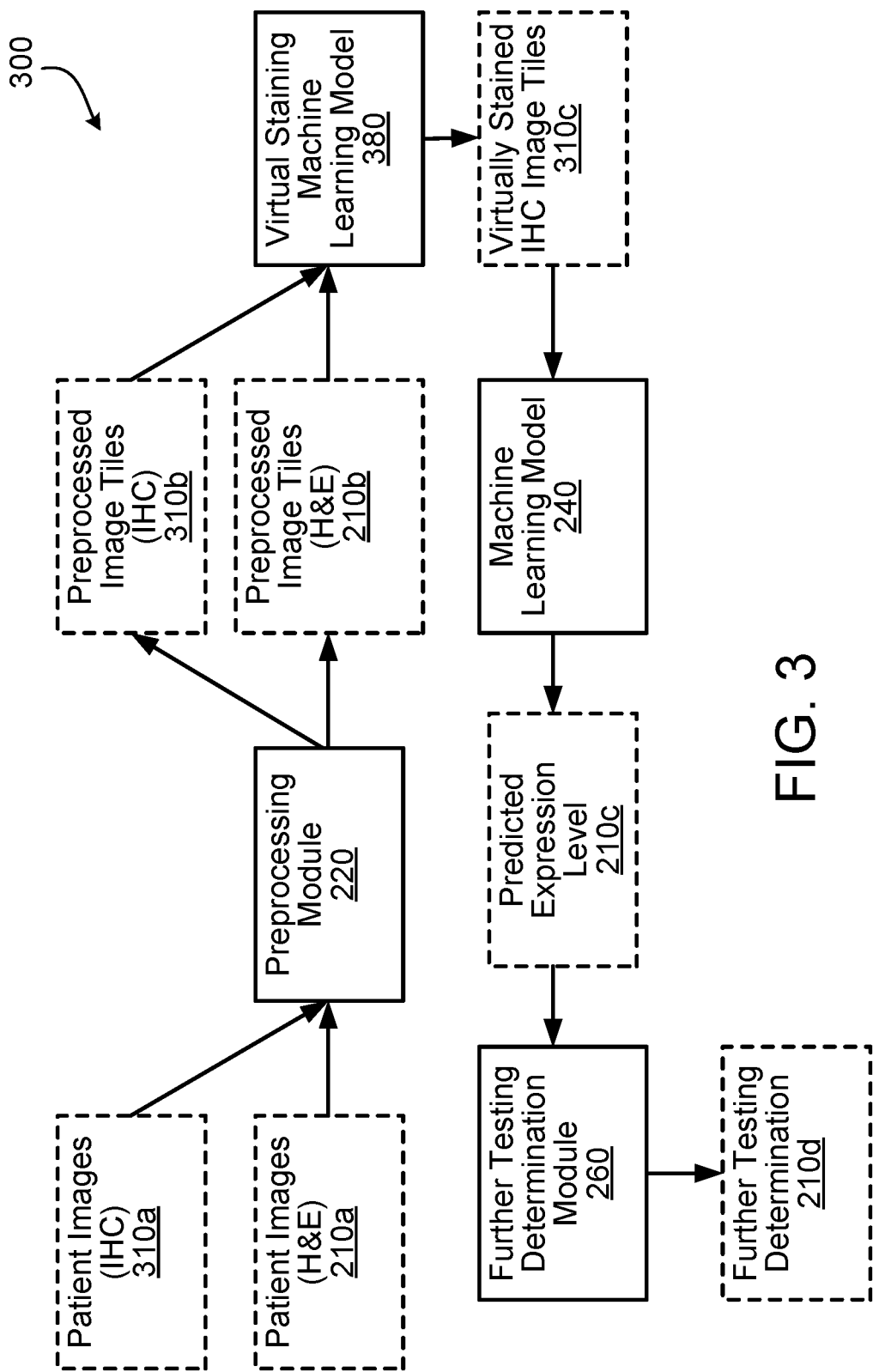
FIG. 3 is a flow diagram illustrating an example architecture for predicting expression levels using a virtual staining machine learning model.

FIG. 3 is a flow diagram illustrating an example architecture 300 for predicting expression levels using a virtual staining machine learning model 380. In the illustrated implementation, architecture 300 includes similar components as the architecture 200 discussed previously with reference to FIG. 2, and also includes a virtual staining machine learning model 380. In some implementations, the machine learning model 380 includes a conditional cycle-GAN model, which can refer to a deep learning model that is capable of learning to map one image domain to another image domain based on paired image data. In the illustrated implementation, the preprocessing module 220 also receives data representing IHC patient images 310a (for example, images of a patients "special" IHC stains, as described previously) and performs the Otsu segmenting and image tiling (and in some implementations, sub-tiling/patching) discussed previously to generate data representing preprocessed IHC image tiles 310b (and, in some implementations, sub-tiles). The virtual staining machine learning model 380 is configured to receive the data representing the preprocessed H&E image tiles 210b and the preprocessed IHC image tiles 310b to virtually IHC stain the preprocessed H&E image tiles 210b using the preprocessed IHC image tiles 310b. As indicated previously, virtual IHC staining can include discovering correlations between an expression of a target protein exhibited in the special IHC stain of the IHC image and the cell morphology exhibited by the H&E image. The virtually stained IHC image tiles 310c are then received by the machine learning model 240 to generate the data indicating the predicted expression level 210c. Because the expression level of target proteins can be derived from the IHC images, virtually staining the preprocessed H&E image tiles 210b can increase the prediction accuracy of the machine learning model 240.

In some implementations, the virtual staining machine learning model 380 is trained by providing the model 380 data representing pairs of H&E images and IHC images so that the model 380 can learn how to transform values of the pixels of the H7E image to different values such that the resulting image approximates an IHC stained image while reserving the cell morphology exhibited by the original H&E images. Each of the approximation and reserving can be measured by loss functions, which can facilitate maximizing the similarity between virtually stained IHC images and real IHC images while minimizing inconsistencies of the cell morphology between the virtually stained IHC images and the original H&E images. If an H&E image and an IHC image are available for the same patient, and pixels of the H&E image and the IHC images can be registered (for example, through an image registration process), the virtual staining model 380 can be trained using methods such as U-nets. If the images are not matched for a patient, or the pixels cannot be registered, the model 380 can be trained using methods like CycleGAN.

Figure 4:
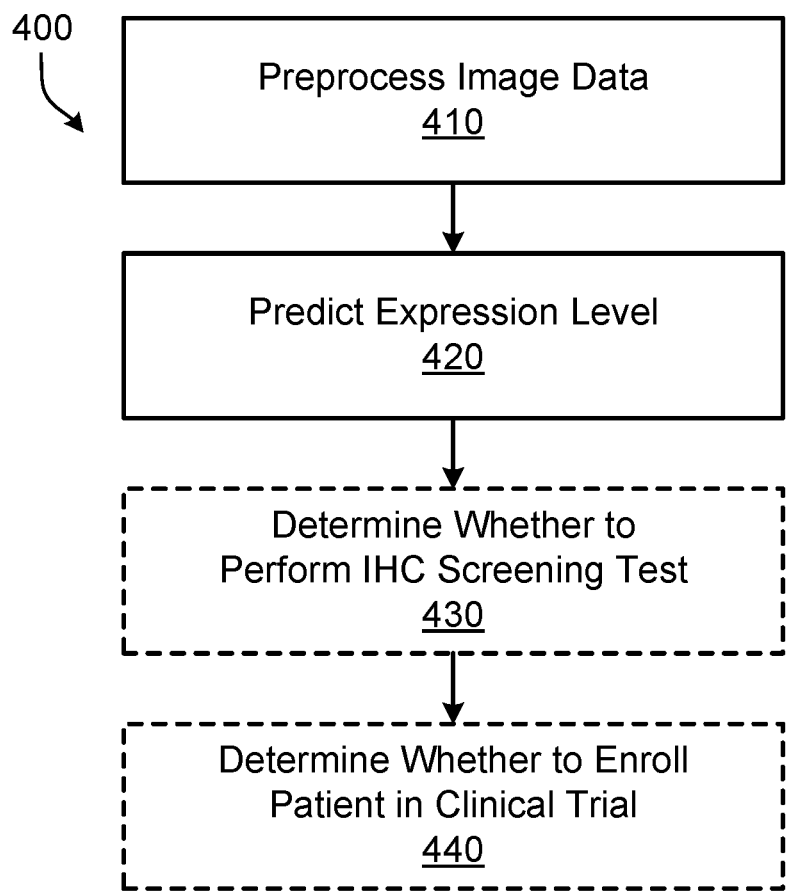
FIG. 4 is a flowchart illustrating an example method for predicting expression levels.

FIG. 4 is a flowchart illustrating an example method 400 for predicting expression levels. In some implementations, the system 100 described earlier with reference to FIG. 1 performs one or more blocks of the method 400. The method 400 includes preprocessing image data (block 410) and predicting an expression level (block 420). In some implementations, the method 400 includes determining whether to perform an IHC screening test (block 430) and determining whether to enroll a patient in a clinical trial (block 440).

At block 410, image data representing a biological image of a patient (for example, an image of an H&E stain) is preprocessed. This can include applying an Otsu thresholding algorithm to segment certain tissues exhibited by the biological image from other components of the medical image. Additionally, or alternatively, preprocessing can include separating the image into a plurality of image tiles. As previously indicated, the image tiles can further be separated into patches (sub-tiles) centered at cell nuclei.

At block 420, a machine learning model is applied to the preprocessed image data to predict an expression level of a target biomarker based on the biological image.

At block 430, the predicted expression level is compared with an expression level threshold to determine whether to perform an IHC screening test for the patient. In some implementations, if the predicted expression level exceeds the expression level threshold, the IHC screening test is performed. If the predicted expression level does not exceed the expression level threshold, the IHC screening test is not performed. For example, the IHC screening test can be performed by a medical expert trained to determined IHC expression proportion scored based on IHC stains.

At block 440, based on the results of the IHC screening test, it is determined whether the patient should be enrolled in a clinical trial.

Figure 5:
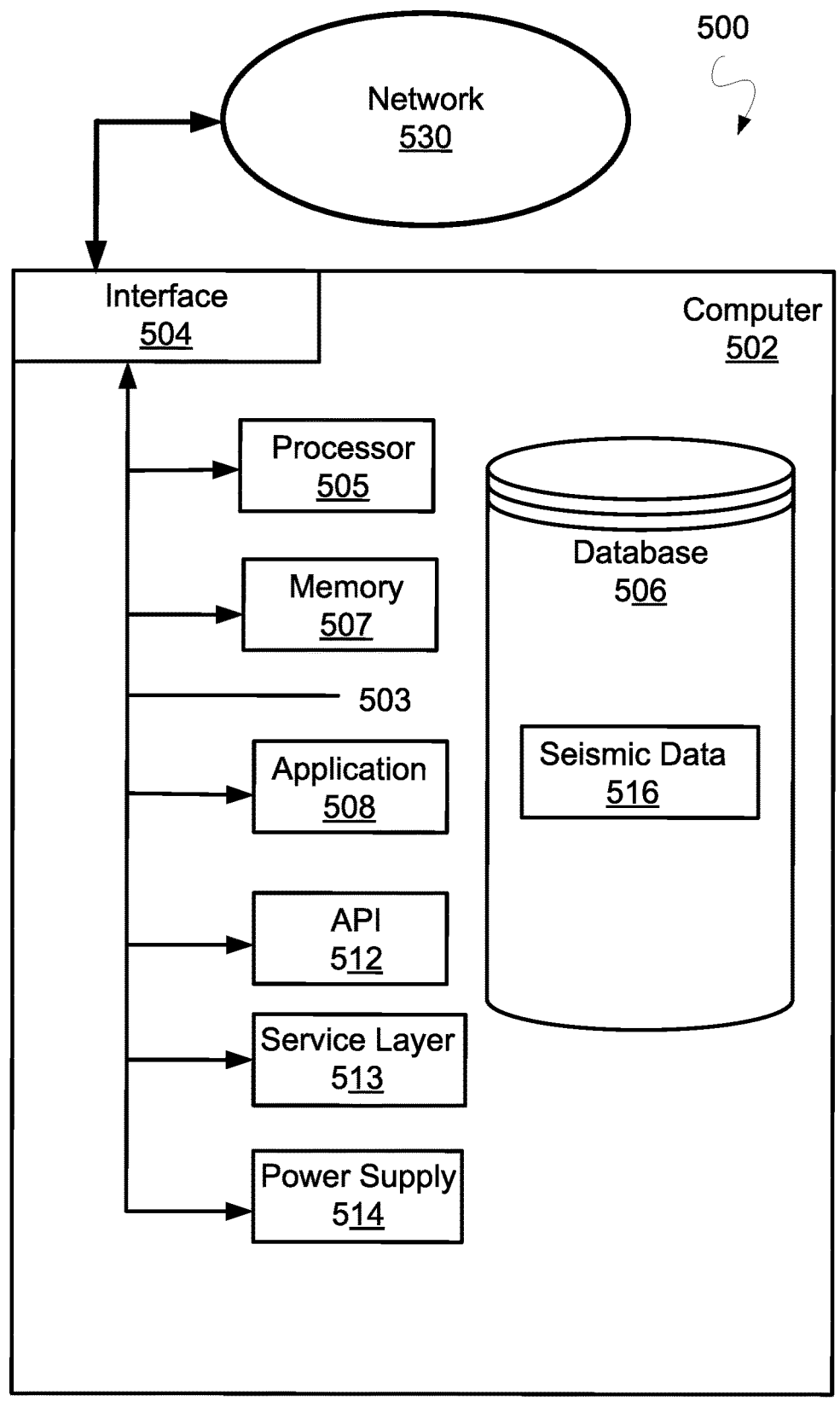
FIG. 5 is a block diagram illustrating an example computer system used to provide computational functionalities associated with described algorithms, methods, functions, processes, flows, and procedures as described in the present disclosure, according to some implementations of the present disclosure.

FIG. 5 is a block diagram of an example computer system 500 used to provide computational functionalities associated with described algorithms, methods, functions, processes, flows, and procedures described in the present disclosure, according to some implementations of the present disclosure. The illustrated computer 502 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 502 can include input devices such as keypads, keyboards, and touch screens that can accept user information. Also, the computer 502 can include output devices that can convey information associated with the operation of the computer 502. The information can include digital data, visual data, audio information, or a combination of information. The information can be presented in a graphical user interface (UI) (or GUI).

The computer 502 can serve in a role as a client, a network component, a server, a database, a persistency, or components of a computer system for performing the subject matter described in the present disclosure. The illustrated computer 502 is communicably coupled with a network 530. In some implementations, one or more components of the computer 502 can be configured to operate within different environments, including cloud-computing-based environments, local environments, global environments, and combinations of environments.

At a high level, the computer 502 is an electronic computing device operable to receive, transmit, process, store, and manage data and information associated with the described subject matter. According to some implementations, the computer 502 can also include, or be communicably coupled with, an application server, an email server, a web server, a caching server, a streaming data server, or a combination of servers.

The computer 502 can receive requests over network 530 from a client application (for example, executing on another computer 502). The computer 502 can respond to the received requests by processing the received requests using software applications. Requests can also be sent to the computer 502 from internal users (for example, from a command console), external (or third) parties, automated applications, entities, individuals, systems, and computers.

Each of the components of the computer 502 can communicate using a system bus 503. In some implementations, any or all of the components of the computer 502, including hardware or software components, can interface with each other or the interface 505 (or a combination of both), over the system bus 503. Interfaces can use an application programming interface (API) 512, a service layer 513, or a combination of the API 512 and service layer 513. The API 512 can include specifications for routines, data structures, and object classes. The API 512 can be either computer-language independent or dependent. The API 512 can refer to a complete interface, a single function, or a set of APIs.

The service layer 513 can provide software services to the computer 502 and other components (whether illustrated or not) that are communicably coupled to the computer 502. The functionality of the computer 502 can be accessible for all service consumers using this service layer. Software services, such as those provided by the service layer 513, can provide reusable, defined functionalities through a defined interface. For example, the interface can be software written in JAVA, C++, or a language providing data in extensible markup language (XML) format. While illustrated as an integrated component of the computer 502, in alternative implementations, the API 512 or the service layer 513 can be stand-alone components in relation to other components of the computer 502 and other components communicably coupled to the computer 502. Moreover, any or all parts of the API 512 or the service layer 513 can be implemented as child or sub-modules of another software module, enterprise application, or hardware module without departing from the scope of the present disclosure.

The computer 502 includes an interface 504. Although illustrated as a single interface 504 in FIG. 5, two or more interfaces 504 can be used according to particular needs, desires, or particular implementations of the computer 502 and the described functionality. The interface 504 can be used by the computer 502 for communicating with other systems that are connected to the network 530 (whether illustrated or not) in a distributed environment. Generally, the interface 504 can include, or be implemented using, logic encoded in software or hardware (or a combination of software and hardware) operable to communicate with the network 530. More specifically, the interface 504 can include software supporting one or more communication protocols associated with communications. As such, the network 530 or the hardware of the interface can be operable to communicate physical signals within and outside of the illustrated computer 502.

The computer 502 includes a processor 505. Although illustrated as a single processor 505 in FIG. 5, two or more processors 505 can be used according to particular needs, desires, or particular implementations of the computer 502 and the described functionality. Generally, the processor 505 can execute instructions and can manipulate data to perform the operations of the computer 502, including operations using algorithms, methods, functions, processes, flows, and procedures as described in the present disclosure.

The computer 502 also includes a database 506 that can hold data (for example, seismic data 516) for the computer 502 and other components connected to the network 530 (whether illustrated or not). For example, database 506 can be an in-memory, conventional, or a database storing data consistent with the present disclosure. In some implementations, database 506 can be a combination of two or more different database types (for example, hybrid in-memory and conventional databases) according to particular needs, desires, or particular implementations of the computer 502 and the described functionality. Although illustrated as a single database 506 in FIG. 5, two or more databases (of the same, different, or combination of types) can be used according to particular needs, desires, or particular implementations of the computer 502 and the described functionality. While database 506 is illustrated as an internal component of the computer 502, in alternative implementations, database 506 can be external to the computer 502.

The computer 502 also includes a memory 507 that can hold data for the computer 502 or a combination of components connected to the network 530 (whether illustrated or not). Memory 507 can store any data consistent with the present disclosure. In some implementations, memory 507 can be a combination of two or more different types of memory (for example, a combination of semiconductor and magnetic storage) according to particular needs, desires, or particular implementations of the computer 502 and the described functionality. Although illustrated as a single memory 507 in FIG. 5, two or more memories 507 (of the same, different, or combination of types) can be used according to particular needs, desires, or particular implementations of the computer 502 and the described functionality. While memory 507 is illustrated as an internal component of the computer 502, in alternative implementations, memory 507 can be external to the computer 502.

The application 508 can be an algorithmic software engine providing functionality according to particular needs, desires, or particular implementations of the computer 502 and the described functionality. For example, application 508 can serve as one or more components, modules, or applications. Further, although illustrated as a single application 508, the application 508 can be implemented as multiple applications 508 on the computer 502. In addition, although illustrated as internal to the computer 502, in alternative implementations, the application 508 can be external to the computer 502.

The computer 502 can also include a power supply 514. The power supply 514 can include a rechargeable or non-rechargeable battery that can be configured to be either user- or non-user-replaceable. In some implementations, the power supply 514 can include power-conversion and management circuits, including recharging, standby, and power management functionalities. In some implementations, the power-supply 514 can include a power plug to allow the computer 502 to be plugged into a wall socket or a power source to, for example, power the computer 502 or recharge a rechargeable battery.

There can be any number of computers 502 associated with, or external to, a computer system containing computer 502, with each computer 502 communicating over network 530. Further, the terms "client," "user," and other appropriate terminology can be used interchangeably, as appropriate, without departing from the scope of the present disclosure. Moreover, the present disclosure contemplates that many users can use one computer 502 and one user can use multiple computers 502.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/-R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of implementations of these systems and methods have been described. However, these systems and methods can include other implementations. For example, although images of certain staining types have been described, other types of staining may be used. For example, some implementations can use Jones stains and Masson's trichrome stains. Although certain types of machine learning architectures have been described, other types of machine learning model can be used. For example, some implementations use conditional CycleGAN machine learning techniques and/or pix2pix machine learning techniques. Although certain diseases have been described, the systems and methods described in this specification can be applicable to several diseases, such as immunological diseases and/or neurological diseases. Although the systems and methods have been described within the context of clinical trials, the systems and methods described can be useful in other contexts, such as virtual multiplex staining for pathology analysis.

What is claimed is:

1. A method performed by one or more computers, the method comprising:
   obtaining image data representing at least one hematoxylin and eosin (H&E)-stained biological image of a patient; and
   processing a model input that comprises the image data representing the at least one H&E-stained biological image using a trained machine learning model to generate, as a model output of the machine learning model, a predicted aggregate expression level of a protein across tissue that is depicted by the at least one H&E-stained biological image, wherein the protein is a biomarker for a particular disease;
   wherein the machine learning model has been trained by performing operations comprising:
      obtaining a set of training examples that each include:
         (i) at least one training H&E-stained biological image; and (ii) a corresponding target aggregate protein expression level across tissue that is depicted by the at least one training H&E-stained biological image; and training the machine learning model on the set of training examples, comprising, for each training example, training the machine learning model to reduce a discrepancy between: (i) a predicted aggregate protein expression level generated by processing the at least one training H&E-stained biological image of the training example using the machine learning model, and (ii) the target aggregate protein expression level specified by the training example; and outputting data identifying the predicted aggregate expression level of the protein.

2. The method of claim 1, further comprising:

determining whether the predicted aggregate expression level of the protein exceeds a threshold expression level; and determining, in response to determining that the predicted aggregate expression level exceeds the threshold expression level, to perform an immunohistochemistry (IHC) screening test for the patient.

3. The method of claim 2, further comprising:

performing the IHC screening test for the patient to determine an IHC score; and determining, based at least partially on the determined IHC score, to enroll the patient in a clinical trial.

4. The method of claim 1, further comprising:

determining whether the predicted aggregate expression level of the protein exceeds a threshold expression level; and determining, in response to determining that the predicted aggregate expression level does not exceed the threshold expression level, to not perform an IHC screening test for the patient.

5. The method of claim 1, further comprising preprocessing the image data by performing an automatic image thresholding process to segment one or more tissue regions of the at least one H&E-stained biological image.

6. The method of claim 1, further comprising preprocessing the image data by separating the at least one H&E-stained biological image into a plurality of image tiles.

7. The method of claim 6, wherein preprocessing the image data comprises separating each of the plurality of image tiles into a plurality of sub-tiles.

8. A system, comprising:

a computer-readable memory comprising computer-executable instructions; and at least one processor configured to execute the computer-executable instructions, wherein when the at least one processor is executing the computer-executable instructions, the at least one processor is configured to carry out operations comprising:

obtaining image data representing at least one hematoxylin and eosin (H&E)-stained biological image of a patient; and processing a model input that comprises the image data representing the at least one H&E-stained biological image using a trained machine learning model to generate, as a model output of the machine learning model, a predicted aggregate expression level of a protein across tissue that is depicted by the at least one H&E-stained biological image, wherein the protein is a biomarker for a particular disease;

wherein the machine learning model has been trained by performing operations comprising:

obtaining a set of training examples that each include: (i) at least one training H&E-stained biological image; and (ii) a corresponding target aggregate protein expression level across tissue that is depicted by the at least one training H&E-stained biological image; and training the machine learning model on the set of training examples, comprising, for each training example, training the machine learning model to reduce a discrepancy between: (i) a predicted aggregate protein expression level generated by processing the at least one training H&E-stained biological image of the training example using the machine learning model, and (ii) the target aggregate protein expression level specified by the training example; and outputting data identifying the predicted aggregate expression level of the protein.

9. The system of claim 8, the operations further comprising:

determining whether the predicted aggregate expression level of the protein exceeds a threshold expression level; and determining, in response to determining that the predicted aggregate expression level exceeds the threshold expression level, to recommend performance of an immunohistochemistry (IHC) screening test for the patient.

10. The system of claim 9, the operations further comprising:

performing the IHC screening test for the patient to determine an IHC score; and determining, based at least partially on the determined IHC score, to enroll the patient in a clinical trial.

11. The system of claim 8, the operations further comprising:

determining whether the predicted aggregate expression level of the protein exceeds a threshold expression level; and determining, in response to determining that the predicted aggregate expression level does not exceed the threshold expression level, to recommend against performance of an IHC screening test for the patient.

12. The system of claim 8, wherein the operations further comprise preprocessing the image data by performing an automatic image thresholding process to segment one or more tissue regions of the at least one H&E-stained biological image.

13. The system of claim 8, further comprising preprocessing the image data by separating the at least one H&E-stained biological image into a plurality of image tiles.

14. The system of claim 13, wherein preprocessing the image data comprises separating each of the plurality of image tiles into a plurality of sub-tiles.

15. One or more non-transitory computer-readable storage media storing instructions executable by one or more processors to cause the processors to perform operations comprising:

obtaining image data representing at least one hematoxylin and eosin (H&E)-stained biological image of a patient; and processing a model input that comprises the image data representing the at least one H&E-stained biological image using a trained machine learning model to generate, as a model output of the machine learning model, a predicted aggregate expression level of a protein across tissue that is depicted by the at least one H&E- stained biological image, wherein the protein is a biomarker for a particular disease;

wherein the machine learning model has been trained by performing operations comprising:

obtaining a set of training examples that each include: (i) at least one training H&E-stained biological image; and (ii) a corresponding target aggregate protein expression level across tissue that is depicted by the at least one training H&E-stained biological image; and training the machine learning model on the set of training examples, comprising, for each training example, training the machine learning model to reduce a discrepancy between: (i) a predicted aggregate protein expression level generated by processing the at least one training H&E-stained biological image of the training example using the machine learning model, and (ii) the target aggregate protein expression level specified by the training example; and outputting data identifying the predicted aggregate expression level of the protein.

16. The one or more non-transitory computer-readable storage media of claim 15, wherein the operations further comprise:

determining whether the predicted aggregate expression level of the protein exceeds a threshold expression level; and determining, in response to determining that the predicted aggregate expression level exceeds the threshold expression level, to perform an immunohistochemistry (IHC) screening test for the patient.

17. The one or more non-transitory computer-readable storage media of claim 15, wherein the operations further comprise:

determining whether the predicted aggregate expression level of the protein exceeds a threshold expression level; and determining, in response to determining that the predicted aggregate expression level does not exceed the threshold expression level, to not perform an IHC screening test for the patient.

18. The one or more non-transitory computer-readable storage media of claim 15, wherein the operations further comprise:

preprocessing the image data by performing an automatic image thresholding process to segment one or more tissue regions of the at least one H&E-stained biological image.

19. The one or more non-transitory computer-readable storage media of claim 15, wherein the operations further comprise:

preprocessing the image data by separating the at least one H&E-stained biological image into a plurality of image tiles.

20. The one or more non-transitory computer-readable storage media of claim 15, wherein the machine learning model comprises a deep neural network.

* * * * *